United States Patent [19]
Daoud

[11] Patent Number: 6,001,393
[45] Date of Patent: Dec. 14, 1999

[54] GINKGO BILOBA EXTRACT ENHANCED BIOAVAILABILITY COMPOSITION AND FOOD PRODUCTS

[76] Inventor: Abdulwahid H. Daoud, P.O. Box 740382, Houston, Tex. 77274-0382

[21] Appl. No.: 08/892,423

[22] Filed: Jul. 14, 1997

Related U.S. Application Data

[63] Continuation of application No. 08/518,476, Aug. 21, 1995, abandoned, which is a continuation of application No. 07/954,842, Sep. 30, 1992, abandoned, which is a continuation of application No. 07/853,227, Mar. 13, 1992, abandoned, which is a continuation of application No. 07/555,427, Aug. 20, 1990, abandoned, which is a continuation of application No. 08/727,329, Oct. 8, 1996, abandoned.

[51] Int. Cl.⁶ .......................................... A61K 9/14
[52] U.S. Cl. ............................... 424/489; 424/455
[58] Field of Search ................... 424/489, 195.1, 424/450, 401; 426/73

[56] References Cited

U.S. PATENT DOCUMENTS

| | | |
|---|---|---|
| 4,708,949 | 11/1987 | Liu . |
| 4,753,929 | 6/1988 | Matsumoto et al. . |
| 4,892,883 | 1/1990 | Chatterjee et al. . |
| 4,981,688 | 1/1991 | Ayroles et al. . |
| 5,389,370 | 2/1995 | O'Reilly et al. . |
| 5,466,455 | 11/1995 | Huffstutler ............... 424/401 |
| 5,512,286 | 4/1996 | Schwabe . |
| 5,525,359 | 6/1996 | Allard et al. ............. 424/499 |
| 5,536,506 | 7/1996 | Majeed et al. ........... 424/464 |
| 5,626,849 | 5/1997 | Hastings et al. ........ 424/195.1 |
| 5,637,316 | 6/1997 | Ribier et al. ............ 424/450 |
| 5,643,623 | 7/1997 | Schmitz et al. ........... 426/73 |

*Primary Examiner*—Thurman K. Page
*Assistant Examiner*—William E. Benston, Jr.
*Attorney, Agent, or Firm*—Michael B. Jolly

[57] ABSTRACT

A composition and method which increases the bioavailability of ingested Ginkgo Biloba extract (GBE). The composition comprises a mixture of polyol(s), and GBE. The composition is ingested, either in the concentrated paste form, diluted with edible liquid or food as an additive. Increased serum levels of gingolide A, B and bilobalide are demonstrated for individuals ingesting the composition over ingesting GBE without the polyol(s).

19 Claims, No Drawings

GINKGO BILOBA EXTRACT ENHANCED BIOAVAILABILITY COMPOSITION AND FOOD PRODUCTS

This application is a continuation of Ser. No. 08/518,476 filed Aug. 21, 1995 which is a continuation of Ser. No. 07/954,842 filed Sep. 30, 1992 abondoned Aug. 21, 1995 which is a continuation of Ser. No. 853,227 filed Mar. 13, 1992 abondoned Sep. 30, 1992, which is a continuation of Ser. No. 07/555,427 filed Aug. 20, 1990 abondoned Mar. 14, 1992 which is a continuation of Ser. No. 08/727,329 filed Oct. 8, 1996 abondoned Sep. 23, 1997.

FIELD OF THE INVENTION

This invention relates to a novel composition of Ginkgo Biloba extract (GBE) and edible polyol or combination of edible polyols which increase the bioavailability of GBE, providing increased serum levels of GBE and decreased urine levels of GBE for a given dose over GBE ingested lacking polyol(s). The composition can be used alone as a concentrate, diluted or as a food or beverage additive.

BACKGROUND OF THE INVENTION

Ginkgo Biloba trees are thought to be the oldest species of tree living, with fossil records dating back more than 200 million years. Surviving ice ages, and incalculable environmental pressures ginkgo tree leaves have evolved to contain a complex mixture of compounds discovered by the ancient chinese in 2800 BC to be useful for treating memory loss. Today, GBE has been the subject of over 300 published studies and reports and is the most frequently prescribed herbal medicine worldwide. GBE is believed to be useful for treating both central nervous system and peripheral circulatory deficiency, useful as an antioxidant in the brain, retina and cardiovascular system, useful for treatment of cerebrovascular insufficiency and other circulatory conditions, and also useful as a PAF inhibitor.

Much attention has been devoted to improving and developing extraction techniques for collecting pure GBE. Schwabe, U.S. Pat. No. 5,512,286 describes an extraction technique suitable for collecting GBE free of serum-precipitating properties. Schwabe, U.S. Pat. No. 5,399,348 describes an extraction procedure which collects GBE free of alkylphenols without the use of chlorinated aliphatic hydrocarbons. O'Reilly, etal. U.S. Pat. No. 5,389,370 discloses an extraction technique which results in a higher active component extract. Ayroles, etal, U.S. Pat. No. 4,981,688 discloses a process for obtaining GBE using organic solvent and removing the proanthocyanidins by precipitation. And Matsumoto, etal, U.S. Pat. No. 4,753,929 describes a procedure for obtaining substantially pure flavone glycosides. Some of these patent holders have also described pharmaceuticals and therapeutic compositions utilizing GBE in addition to Chatterjee, etal, U.S. Pat. No. 4,892,883 and Liu, U.S. Pat. No. 4,708,949 and others. This prior art coupled with the numerous published articles addressing GBE therapeutic qualities exemplifies the need to increase the efficiency and availability of the prized GBE. The inventor has recognized the need for increasing the bioavailability and efficiency of ingested GBE so that a higher percent of the GBE ingested will actually be utilized instead of being eliminated. Majeed, etal., U.S. Pat. No. 5,536,506 discloses the use of piperine to increase the bioactivity of nutritional compounds, such as GBE. In contrast to the present invention the Majeed invention utilizes a relatively rare extract, piperine whose drug bioavalability enhancement mechanism is unknown, while the present invention utilizes readily available edible polyols as an additive to increase gastrointestinal absorption of ingested GBE. The GBE polyol composition may be ingested either alone or in combination with other additives, as a concentrate, diluted, encapsulated, elixir formula, or as a food and beverage additive.

DETAILED DESCRIPTION OF THE PREFERRED EMBODIMENT

The bioavailability enhancement of ingested commercially available GBE is provided by the addition of an edible polyol or combination of edible polyols with powdered GBE being mixed with the polyol(s) forming a concentrated solution of GBE and polyol(s). The solution may also be formed in the presence of water or other edible liquid(s) if desired. The concentrated solution may be incorporated into a beverage formulation, food product, over the counter nutritional supplement and other food products. The concentrated solution may also be added to the food product in an amount which, when consumed, would provide ingestion of a therapeutically effective amount of GBE.

The inventor contemplates the use of commercially available GBE, extracted from Ginkgo Biloba tree leaves, utilizing one of the numerous extraction techniques described in the prior art set forth above. GBE is commercially sold in a powder form with active compound approximate concentrations as set forth below:

Flavone Glycosides 25.5%
Terpenelcatones* 6.4%
  * Terpenelcatones include the following:
  Gingolide A 2.4%
  Gingolide B 1.2%
  Gingolide C 1.5%
  Bilobalide 1.3%

GBE used by the inventor for carrying out his invention contained the above concentration of components as disclosed by the supplier, the use of GBE from other sources may include slightly different compound concentrations, however variations in these concentrations will not alter the effectiveness of the present invention.

An edible polyol or number of polyols are selected for forming the concentrated solution. One or more of the numerous commercially available polyols may be employed, including: xylitol, iditol, maltitol, sorbitol, mannitol, dulcitol, inositol, erythritol, lactitol, glycerin, and propylene glycol. The preferable polyol being USP or food grade glycerin, since this polyol is a natural food product as desired by many consumers of this type product. The polyol(s) chosen will perform equivalently, limited only by variations of concentrations used and heating and mixing time variations depending upon the polyol, combination of polyols, or polyol solution.

Solubilization of the GBE may be carried out either in polyol(s) alone, with edible liquid and polyol(s), or with edible liquid followed by adding polyol(s). The inventor believes the mechanism which provides the effectiveness of this invention involves solubilization of the powdered GBE with the polyol. The polyol(s) provides the necessary —OH groups which, upon heating and mixing with the powdered GBE enhances the solubility of GBE providing the medium or condition for dissociation of inter- and intramolecular complexes and aggregates thus providing a higher concentration of GBE molecular species available for gastrointestinal absorption.

If a concentrated paste is desired the polyol is first added to the powdered GBE and heated while mixing the solution.

The polyol(s) may be about 1 to about 99 percent of the polyol(s)/GBE solution. The solution is heated to about 60° C. while mixing until the solution becomes a translucent paste. The concentrated paste may be ingested alone, added to food or beverages, encapsulated or added to an elixir formula. The concentrated paste is also most suitable as an additive for chewing gum, candy and other foods products which are normally semi solid or solid.

The solution may also be formed in the presence of water of other edible liquid in a concentration of about 0 to about 99 percent. The edible liquid may be water, dairy products, fruit juice, vegetable juice, soft drinks, carbonated drinks, nutritional supplement drinks, fermented beverages, liquors, teas, coffees and other liquids normally consumed by people.

The inventor prepared a solution using the preferred glycerin, the glycerin was added to water to about a preferred 25% glycerin water solution. The glycerin water concentration may vary from about 1% to about 100% glycerin, depending upon the amount of GBE used, without altering the effectiveness of the invention. About 25 grams of the powdered GBE was then added to 100 ml of the glycerin water solution. The GBE, glycerin, and water solution was then heated to about 50–80° C. and mixed for about 5–20 minutes. Heating and mixing may vary depending upon ambient conditions, upon the amount and type of polyol(s) chosen and the amount of GBE added to the solution. The heating and mixing steps are particularly important to assure complete dissociation and solubilization of the GBE in the polyol/water solution. The inventor has found that ingestion of the GBE/polyol/water composition results in increased levels of gingolide A, B, and bilobalide measured in the blood serum of an individuals who ingest the composition over the levels of gingolide A, B, and bilobalide measured in the blood serum of individuals who ingested GBE without the polyol composition. The same individuals also showed decreased levels of the GBE active compounds in their urine when ingesting GBE/polyol rather than GBE alone.

In an experiment six individuals whose body weights ranged between 155 and 165 lbs. ingested 120 mg of powdered GBE (containing: 2.88 mg Gingolide A, 1.44 mg Gingolide B, and 1.56 mg Bilobalide). Three of the individuals ingested the GBE dose mixed in water, while the other three individuals ingested the GBE dose which was first prepared with glycerine as described above. Blood serum and urine was then collected from the individuals at specific time intervals, and analyzed using a standard HPLC method for the active compound concentrations. The results are recorded in Tables I, II, III, and IV. The results of the experiment illustrate the desired increased levels of GBE active compounds for longer periods of time over the levels measured in persons who ingest GBE without the GBE/polyol/water composition. The results also indicate that the added glycerin decreases the amount of time before the maximum level of extract component enters the individuals serum.

The concentrated composition may be added to numerous food or beverage products. The inventors contemplates adding the concentration to snack foods, chewing gum, candy, nutrition bars, canned or bottled beverages, fruit juices, nutritional drinks and foods. The amount of GBE ingested in a particular food or beverage, which has the concentration added may equal a therapeutically effective dose of GBE. A therapeutically effective dose as described in the prior art, may be between 60 and 240 mg of GBE per day, however this amount may vary depending the individual.

I claim:

1. A composition for increasing the bioavailability of ingested ginkgo biloba extract GBE where the GBE is provided in powdered form and contains from about 22 to about 27 percent flavone glycosides and from about 4 to about 8 percent terpenelcatones, the composition comprised of;
    a) an edible polyol or a combination of one or more edible polyols wherein the polyol(s) are between about 1 and about 99 percent of the composition are heated and mixed with the GBE forming a GBE/polyol(s) combination until the powdered GBE is solubilized forming a concentrated GBE/polyol(s) solution.

2. The composition as set forth in claim 1 wherein the edible polyol is one or more of the polyols selected from a group consisting of: xylitol, iditol, maltitol, sorbitol, mannitol, dulcitol, inositol, erythritol, lactitol, glycerin, USP glycerin, food grade glycerin and propylene glycol.

3. The composition as set forth in claim 1 wherein said polyol(s) is diluted with an edible liquid wherein said polyol(s) comprises about 1 to about 99 percent of the edible liquid/polyol dilution.

4. The composition as set forth in claim 3 wherein said edible liquid is one or more of the liquids consisting of: water, dairy products, fruit juice, vegetable juice, soft drinks, carbonated drinks, nutritional supplement drinks, fermented beverages, teas, and coffees.

5. The composition as set forth in claim 1 wherein said composition is added to food.

6. The composition as set forth in claim 1 wherein said composition is added to an edible liquid or food in a therapeutically effective amount.

7. A method for increasing the amount of ginkgo biloba extract (GBE) chemical constituents in an individual's blood serum over the amount of GBE measured in an individual's blood serum when the individual has ingested GBE without a polyol additive, comprising the steps:
    a) adding about 1% to about 99% of an edible polyol or combination of edible polyols to about 99% to about 1% of powdered GBE,
    b) heating and mixing the GBE/polyol(s) combination until the powdered GBE is solubilized forming a concentrated GBE/polyol(s) solution,
    c) ingesting the GBE/polyol(s) solution.

8. The method as set forth in claim 7 further comprising the step: adding an edible liquid prior to or after step (a) and or step (b) and in an amount of about 0% to about 99% of the composition.

9. The method as set forth in claim 7 wherein the method further increases the amount of gingolide A in the individual's blood serum.

10. The method as set forth in claim 7 wherein the method further increases the amount of gingolide B in the individual's blood serum.

11. The method as set forth in claim 7 wherein the method further decreases the amount of gingolide B in the individual's urine.

12. The method as set forth in claim 7 wherein the method further decreases the amount of bilobalide in the individual's urine.

13. The method as set forth in claim 7 wherein the polyol is one or more of the polyols selected from a group consisting of: xylitol, iditol, maltitol, sorbitol, mannitol, dulcitol, inositol, erythritol, lactitol, glycerin, USP glycerin, food grade glycerin, and propylene glycol.

14. The method as set forth in claim 7 wherein the combination of polyol(s) and GBE, prior to ingesting is added to a beverage or food.

15. A method for increasing the bioavailability of ginkgo biloba extract where the extract contains about 25% flavone glycosides and about 6% terpenelcatones, the method comprising the steps;

a) adding ginkgo extract to an edible polyol or combination of edible polyol(s), forming a ginkgo extract and polyol(s) combination, wherein said ginkgo extract is between about 1 and about 99 percent of the combination and the polyol(s) is between about 1 and 99 percent of the combination, b) heating and mixing the ginkgo extract, and polyol(s) combination until the extract becomes solubilized by the polyol(s), and c) ingesting the ginkgo extract/polyol(s) solution.

16. The method as set forth in claim 15 further comprising the step: adding an edible liquid either to the polyol(s), ginkgo extract, or ginkgo extract/polyol(s) combination prior to, during, or after step (a) and or step (b).

17. The method as set forth in claim 15 further comprising the step: adding the solution formed from step (a) to an edible liquid or food prior to step (c).

18. The method as set forth in claim 15 wherein the method further comprises the step: adding the ginkgo extract and polyol(s) solution, prior to ingesting, to an edible liquid or food in a therapeutically effective amount.

19. The method as set forth in claim 15 wherein the polyol is one or more of the polyols selected from a group consisting of: xylitol, iditol, maltitol, sorbitol, mannitol, dulcitol, inositol, erythritol, lactitol, glycerin, USP glycerin, food grade glycerin and propylene glycol.

TABLE I

Ginkgolide A, average concentration in ng/mL
in blood serum of three individuals
taken at different times, where Column A
represents the average concentration
measured in three individuals who ingested 120 mg of
powered GBE mixed in water
and Column B represents the average concentration
measured in three individuals
who ingested 120 mg of powdered GBE solubilized
with glycenne and water combination.

| TIME | A<br>PLAIN GBE (conc) | B<br>GLYCERINE/GBE (conc) |
| --- | --- | --- |
| 15 minutes | 2.5 | 5.00 |
| 30 minutes | 10.3 | 17.1 |
| 45 minutes | 23.8 | 35.0 |
| 1 hour | 35.0 | 62.0 |
| 1.5 hours | 42.0 | 55.2 |
| 2.0 hours | 32.0 | 47.2 |
| 2.5 hours | 23.2 | 38.7 |
| 3.0 hours | 10.3 | 30.2 |
| 4.0 hours | 6.0 | 21.3 |
| 6.0 hours | 4.9 | 12.0 |
| 9.0 hours | 2.1 | 7.30 |
| 12.0 hours | 1.3 | 6.00 |
| 15.0 hours | 1.1 | 4.90 |
| 18.0 hours | 1.0 | 4.00 |
| 24.0 hours | 0.5 | 4.00 |
| 30.0 hours | 0.5 | 3.00 |
| 36.0 hours | 0.3 | 2.00 |

TABLE II

Ginkgolide B, average concentration in ng/mL
in blood serum of three individuals
taken at different times, where Column A
represents the average concentration
measured in three individuals who ingested 120 mg of
powered GBE mixed in water
and Column B represents the average concentration
measured in three individuals
who ingested 120 mg of powdered GBE solubilized
with glycerine and water combination.

| TIME | A<br>PLAIN GBE (conc) | B<br>GLYCERINE/GBE (conc) |
| --- | --- | --- |
| 15 minutes | 1.10 | 2.50 |
| 30 minutes | 5.00 | 9.00 |
| 45 minutes | 7.50 | 15.0 |
| 1 hour | 11.1 | 19.3 |
| 1.5 hours | 14.6 | 20.1 |
| 2.0 hours | 12.1 | 17.2 |
| 2.5 hours | 8.10 | 15.0 |
| 3.0 hours | 5.10 | 12.5 |
| 4.0 hours | 2.90 | 7.60 |
| 6.0 hours | 1.50 | 5.00 |
| 9.0 hours | 1.10 | 3.00 |
| 12.0 hours | 1.00 | 2.00 |
| 15.0 hours | 1.00 | 1.20 |
| 18.0 hours | 0.70 | 1.00 |
| 24.0 hours | 0.43 | 1.00 |
| 30.0 hours | | |
| 36.0 hours | | |

TABLE III

Bilobalide, average concentration in ng/mL
in blood serum of three individuals taken at
different times, where Column A
represents the average concentration measured in
three individuals who ingested 120 mg of
powered GBE mixed in water and Column B
represents the average concentration measured in
three individuals who ingested 120
mg of powdered GBE solubilized with
glycerine and water combination.

| TIME | A<br>PLAIN GBE (conc) | B<br>GLYCERINE/GBE (conc) |
| --- | --- | --- |
| 15 minutes | 2.50 | 4.700 |
| 30 minutes | 5.20 | 10.10 |
| 45 minutes | 7.20 | 15.20 |
| 1 hour | 10.0 | 16.30 |
| 1.5 hours | 10.7 | 15.10 |
| 2.0 hour | 8.10 | 12.10 |
| 2.5 hours | 6.20 | 10.02 |
| 3.0 hours | 4.15 | 6.200 |
| 4.0 hours | 2.30 | 4.100 |
| 6.0 hours | 2.00 | 2.800 |
| 9.0 hours | 1.30 | 2.000 |
| 12.0 hours | 0.80 | 1.150 |
| 18.0 hours | 0.50 | 0.900 |
| 24.0 hours | | 0.750 |
| 30.0 hours | | 0.500 |
| 36.0 hours | | |

TABLE IV

Summary of results of Tables I, II, III including % GBE dose in Urine

| Treatment | Max ng/mL serum | Tmax* | % Dose in Urine |
| --- | --- | --- | --- |
| Plain Ginkgolide A | 42.25 | 1.3 | 75% |
| Glycerine Ginkgolide A | 62.75 | 1.02 | 62% |
| Plain Ginkgolide B | 15.11 | 1.35 | 41.3% |
| Glycerine Ginkgolide B | 21.25 | 1.15 | 33.2% |
| Plain Bilobalide | 11.3 | 1.35 | 31.15% |
| Glycerine Bilobalide | 17.21 | 1.12 | 25.7% |

*Tmax = The time at which a maximum serum level concentration was measured in the individuals.

* * * * *